(12) United States Patent
Qureshi et al.

(10) Patent No.: US 9,034,230 B2
(45) Date of Patent: May 19, 2015

(54) METHOD FOR MAKING AN ELASTOMERIC APERTURED WEB

(75) Inventors: Khalid Qureshi, Mason, OH (US); Edward Lawrence Schmidt, Jr., Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 420 days.

(21) Appl. No.: 12/534,353

(22) Filed: Aug. 3, 2009

(65) Prior Publication Data

US 2011/0024940 A1    Feb. 3, 2011

(51) Int. Cl.
| | |
|---|---|
| B29C 65/00 | (2006.01) |
| B29C 55/18 | (2006.01) |
| A61F 13/15 | (2006.01) |
| A61F 13/514 | (2006.01) |
| B26F 1/20 | (2006.01) |
| B29L 9/00 | (2006.01) |

(52) U.S. Cl.
CPC ............ B29C 55/18 (2013.01); A61F 13/15707 (2013.01); A61F 13/5146 (2013.01); A61F 13/51462 (2013.01); A61F 13/51464 (2013.01); B26F 1/20 (2013.01); B29L 2009/00 (2013.01)

(58) Field of Classification Search
USPC ........................................................ 264/154
See application file for complete search history.

(56) References Cited

U.S. PATENT DOCUMENTS

| | | | |
|---|---|---|---|
| 3,496,259 A | 2/1970 | Guenther | |
| 3,965,906 A | 6/1976 | Karami | |
| 4,223,059 A | 9/1980 | Schwarz | |
| 4,438,167 A | 3/1984 | Schwarz | |
| 5,156,793 A | 10/1992 | Buell et al. | |
| 5,167,897 A | 12/1992 | Weber et al. | |
| 5,202,173 A | 4/1993 | Wu et al. | |
| 5,254,111 A | 10/1993 | Cancio et al. | |
| 5,296,184 A | 3/1994 | Wu et al. | |
| 5,354,597 A | 10/1994 | Capik et al. | |
| 6,258,308 B1 | 7/2001 | Brady et al. | |

(Continued)

FOREIGN PATENT DOCUMENTS

| | | |
|---|---|---|
| JP | 06-328600 A | 11/1994 |
| WO | WO 92/15444 | * 9/1992 |

(Continued)

OTHER PUBLICATIONS

International Search Report dated Oct. 26, 2010, 4 pages.

(Continued)

*Primary Examiner* — Larry Thrower
(74) *Attorney, Agent, or Firm* — Jeffrey V Bamber; Jay A Krebs

(57) ABSTRACT

A method for making an elastomeric apertured web comprises providing a precursor web comprising a laminate which is subjected to incremental stretching to form an elastomeric precursor web. A forming apparatus is provided comprising a first member and a second member, wherein the first member comprises a mating member, and the second member comprises teeth which are joined to the second member. The elastomeric precursor web is moved through the forming apparatus, wherein apertures are formed in the elastomeric precursor web material as the teeth on the second member penetrate the mating member forming an elastomeric apertured web. The elastomeric apertured web exhibits a WVTR of at least about 1000 g/m$^2$/day.

23 Claims, 8 Drawing Sheets

(56) References Cited

U.S. PATENT DOCUMENTS

| | | | |
|---|---|---|---|
| 6,368,444 B1 | 4/2002 | Jameson et al. | |
| 6,794,023 B1 | 9/2004 | Melik et al. | |
| 6,811,643 B2 | 11/2004 | McAmish et al. | |
| 6,821,612 B1 | 11/2004 | Melik et al. | |
| 6,843,949 B2 | 1/2005 | Brady et al. | |
| 8,158,043 B2 | 4/2012 | Gibson et al. | |
| 2006/0087053 A1* | 4/2006 | O'Donnell et al. | 264/156 |
| 2008/0224351 A1 | 9/2008 | Curro et al. | |
| 2009/0127742 A1 | 5/2009 | Qureshi et al. | |
| 2010/0201024 A1 | 8/2010 | Gibson et al. | |
| 2012/0049404 A1 | 3/2012 | Gibson et al. | |

FOREIGN PATENT DOCUMENTS

| | | |
|---|---|---|
| WO | WO-2005/052052 | 6/2005 |
| WO | WO-2005/097031 | 10/2005 |
| WO | WO-2008/120959 A1 | 10/2008 |

OTHER PUBLICATIONS

USPTO Office Action dated Oct. 29, 2009, U.S. Appl. No. 12/366,825, filed Feb. 6, 2009, first named inventor Fredrick William Gibson, 13 pgs.

USPTO Office Action dated May 17, 2010, U.S. Appl. No. 12/366,825, filed Feb. 6, 2009, first named inventor Fredrick William Gibson, 16 pgs.

USPTO Office Action dated Nov. 24, 2010, U.S. Appl. No. 12/366,825, filed Feb. 6, 2009, first named inventor Fredrick William Gibson, 16 pgs.

* cited by examiner

METHOD FOR MAKING AN ELASTOMERIC APERTURED WEB

FIELD OF THE INVENTION

The present invention relates to methods for making apertured webs. Specifically, the method can be used to make elastomeric apertured laminates.

BACKGROUND OF THE INVENTION

A consumer need which underlies the development in the absorbent article field, in particular disposable diapers, is the need for products providing both high protection and comfort. Comfort benefits are provided in diaper by introducing materials that are breathable and that stretch in order to conform to the body of the wearer during use. Breathability and stretchability have typically concentrated on the incorporation of breathable backsheet covers that are vapor permeable and side panels that stretch and conform to the body of the wearer.

Backsheet covers on diapers are designed to be fluid impermeable to prevent leakage and vapor permeable to provide comfort. Backsheet covers typically incorporate microporous films that are impervious to liquids but are vapor permeable to allow gaseous exchange with the environment. Microporous films have limited stretchability; therefore, separate stretchable side panels are required to deliver stretch.

Stretchable side panels are often laminates composed of elastic films and extensible nonwovens. The film and nonwoven laminates are activated by incremental stretching to form an elastic laminate. Although elastic film and nonwoven laminates stretch to conform to the body of the wearer, they have limited breathability.

There is the need for backsheet outer cover that is stretchable for conforming fit and vapor permeable for providing breathability. Accordingly, there is a need for a process for producing a stretchable laminate that is vapor permeable resulting in a breathable elastic laminate having a WVTR greater than about 1000 g/m$^2$/day.

SUMMARY OF THE INVENTION

A method for making elastomeric apertured web is disclosed which is suitable for use as the outer cover of a disposable absorbent article. The method comprises providing a precursor web comprising a zero strain laminate comprising a substantially untensioned first elastomeric ply secured to a substantially untensioned second extensible ply comprising a continuous web. The precursor web is subjected to incremental stretching whereby the second ply is permanently elongated forming an elastomeric precursor web. A forming apparatus is provided comprising a first member and a second member, wherein the first member comprises a mating member, and the second member comprises teeth being tapered from a base and a tip, the teeth being joined to the second member at the base. The elastomeric precursor web is moved through the forming apparatus, wherein apertures are formed in the elastomeric precursor web material as the teeth on the second member penetrate the mating member forming an elastomeric apertured web. The elastomeric apertured web exhibits a WVTR of at least about 1000 g/m$^2$/day.

In one embodiment the pair of intermeshing members comprises a pair of counter-rotating, intermeshing rollers. The pair of intermeshing rollers comprises a first roller having circumferentially-extending ridges and grooves, and a second roller having teeth which mesh with the grooves of the first roller. The teeth are tapered from a base to a tip and are joined to the second roller at the base. The elastomeric precursor web is moved through a nip of the counter-rotating, intermeshing rollers where apertures are formed in the precursor web material as the teeth on one of the rollers intermesh with grooves on the other of the rollers.

DETAILED DESCRIPTION OF THE INVENTION

Definitions

Figure 1:
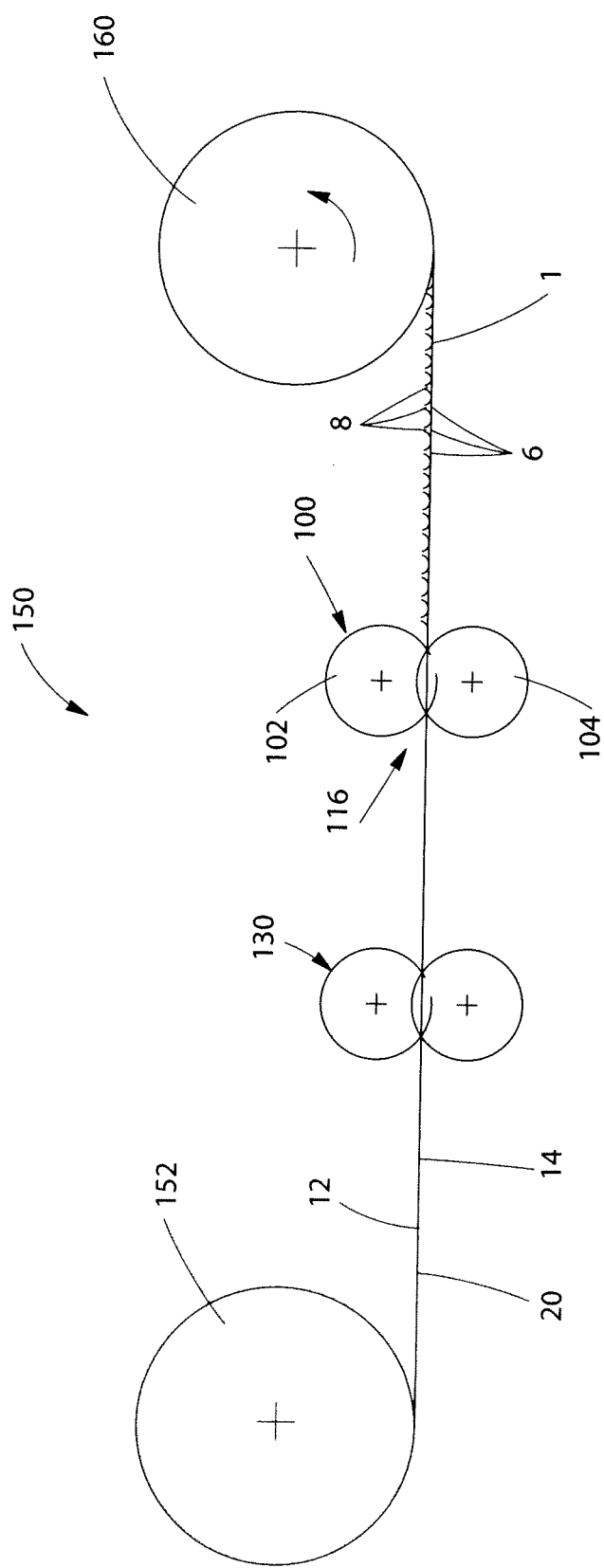
FIG. 1 is a schematic representation of a process of the present invention.

As used herein and in the claims, the term "comprising" is inclusive or open-ended and does not exclude additional unrecited elements, compositional components, or method steps.

As used herein "depth of engagement" means the extent to which intermeshing teeth and grooves of opposing activation members extend into one another.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, and bonded carded web processes, including carded thermal bonding. The basis weight of nonwoven fabrics is usually expressed in grams per square meter (gsm). The basis weight of the laminate web is the combined basis weight of the constituent layers and any other added components. The basis weight of laminate webs suitable for use in the present invention can range from 6 gsm to 400 gsm, depending on the ultimate use of the web. For use as a hand towel, for example, both a first web and a second web can be a nonwoven web having a basis weight of between 18 gsm and 500 gsm.

Fiber diameters are usually expressed in microns; fiber size can also be expressed in denier, which is a unit of weight per length of fiber.

The constituent fibers of a nonwoven web can be polymer fibers, and can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven web may also be a mixture of different fiber types, differing in such features as chemistry (e.g. PE and PP), components (mono- and bi-), denier (micro denier and >20 denier), shape (i.e. capillary and round) and the like. The constituent fibers can range from about 0.1 denier to about 100 denier.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible stereochemical configurations i.e. isotactic, atactic, and syndiotactic.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multi-constituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

"Absorbent article" means devices that absorb and/or contain liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like.

"Activation" is the mechanical deformation of one or more portions of an extensible material (e.g., film, nonwoven, fiber) that results in permanent elongation of the extensible material in the direction of activation in the X-Y plane of the material. Activation of a laminate that includes an elastic material joined to an extensible material typically results in one or more portions of the extensible material being at least partially permanently elongated, while the elastic material returns substantially to its original dimension. "Activated" means a material that has been subjected to an activation process. Suitable examples of absorbent articles, absorbent article components and processes for activation can be found in U.S. Pat. Nos. 5,156,793; 4,438,167; 5,202,173; 5,254,111; 5,296,184; 5,354,597; 6,258,308; 6,368,444; 6,811,643; 6,821,612; 6,843,949; and 6,794,023.

"Direction of Activation" means the direction in which the material is stretched in the X-Y plane during the activation process. For laminates comprising elastic materials laminated to extensible nonwovens or films, the direction of activation is also the direction in which the laminate is capable of stretching after completion of the activation process. For materials that do not exhibit elastic behavior, the direction of activation refers to the direction of the dimension in the X-Y plane of the material that is increased most as a result of the activation process. Examples of directions of activation include the machine direction, the cross direction, the longitudinal direction, the lateral direction, and diagonal direction.

"Unactivated" refers to a material that has not been subjected to mechanical deformation process that imparts extensibility to the material.

"Disposed" refers to the placement of one element of an article relative to another element of an article. For example, the elements may be formed (joined and positioned) in a particular place or position as a unitary structure with other elements of the diaper or as a separate element joined to another element of the diaper."

An "elastomeric or elastic material" is a material (e.g., film, fiber, nonwoven, laminate or combinations of these) that elongates, without substantial rupture or breakage, to 50% in the Hysteresis Test fully described below. Further, the elastic material has set less than or equal to 20% as measured according to the Hysteresis Test. For example, an elastic material that has an initial length of 25 mm can elongate to at least 37.5 mm (50% elongation and, have a set of 10% (i.e. length=27.5 mm) when subjected to the Hysteresis Test. Micro-sized rupture or breakage of a material is not considered substantial rupture or breakage, and in some cases may occur as part of the extensibility mechanism of the material. However, macro-sized ruptures through the structure (e.g. one or more large tears such as tears greater than about 5 mm in any direction, or breaking into two or more pieces or resulting in significant structural degradation which may render the material unusable for its intended purpose) are considered substantial ruptures or breakage.

"An extensible" material is a material that elongates, without substantial rupture or breakage, to 50% in the Hysteresis Test. Further, the material has set greater than 20% as measured according to the Hysteresis Test. For example, an extensible material that has an initial length of 25 mm can elongate at least to 37.5 mm (50% elongation) and have a set of 40% (length=35 mm) when subjected to the Hysteresis Test.

"A stretchable" material is a material that elongates, without substantial rupture or breakage, to 50% in the Hysteresis Test. A stretchable material may be elastomeric or extensible as previously defined. A non-stretchable material is a material that does not elongate, without substantial rupture or breakage, to 50% in the Hysteresis Test.

"Film" refers, to a relatively nonporous, non-fibrous material made by a process that includes extrusion of, e.g., a polymeric material through a relatively narrow slot of a die. Films are less than 1 mm in thickness. The ratio of X and Y dimensions of a film to the thickness are greater than 100:1. The polymeric film may be impervious to a liquid and pervious to an air vapor, but need not necessarily be so. Suitable examples of film materials are described in more detail below.

"Garment-facing side" refers to the outermost portion of an element of a wearable absorbent article when the absorbent article is worn as intended. The opposing side, or innermost portion, of the same element is referred to as the "wearer-facing side." It is to be understood that the garment-facing side and the wearer-facing side of an element are relative to the wearer of the article with the garment-facing side being furthest from the wearer and the wearer-facing side being closest to the wearer. In the example of a typical disposable diaper, the portion of the outer cover that faces away from the wearer is the garment-facing side while the opposing side of the outer cover is the wearer-facing side.

"Joined" refers to configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by methods known in the art, e.g. adhesive bonding, thermal bonding, ultrasonic bonding.

"Zero-strain laminate web" refers to a laminate web comprised of at least two plies of material which are secured to one another, either intermittently or substantially continuously, along at least a portion of their coextensive surfaces while in a substantially untensioned (zero strain) condition. Some examples of intermittent bonding are spiral or melt-blown gluing, printing, etc. Some examples of continuous bonding are slot coating, printing, etc. One of the plies employed in a zero-strain laminate web is comprised of a material which is elastomeric. The second ply secured to the elastomeric ply is extensible.

"Leg Band" refers to a distinct elasticized element or region adjacent the longitudinal side edge of the article in at least a portion of the crotch region of the article. The leg band may be elastically contracted and serves to provide a snug fit of the article around at least a portion of a wearer's leg. The leg band may comprise a separate element attached to a surface of the article or may comprise portions of the article, such as a topsheet, backsheet, outer cover, or inner leg cuff material.

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the web as it moves through the manufacturing process. Directions within ±45 degrees of the MD are considered to be machine directional. The "cross machine direction" or "CD" is the direction substantially perpendicular to the MD and in the plane generally defined by the web. Directions within 45 degrees of the cross direction are considered to be cross directional.

"Nonwoven" refers to a porous, fibrous material made from continuous (long) filaments (fibers) and/or discontinuous (short) filaments (fibers) by processes such as spunbonding, meltblowing, carding, and the like. Nonwovens do not have a woven or knitted filament pattern. Nonwovens may be liquid permeable or impermeable.

"Outboard" and "inboard" refer, respectively, to the location of an element disposed relatively far from or near to the longitudinal centerline of an absorbent article with respect to a second element. For example, if element A is outboard of element B, then element A is farther from the longitudinal centerline than is element B.

"Outer Cover" refers to the layer of the article that is furthest from the skin of a wearer when the article is worn. The outer cover may comprise a single material, a laminate (e.g., may comprise separate, but joined, materials in the Z direction), or a composite material (e.g., may comprise separate, but joined, materials in the X and/or Y directions). A stretchable outer cover is stretchable at least in some portions of the outer cover. Generally, an elastically stretchable outer cover laminate includes a soft, cloth-like material on the garment-facing surface of the outer cover and an elastic material in at least a portion of the laminate. A second soft, cloth-like material may be included on the wearer-facing surface of the outer cover.

"Web" means a material capable of being wound into a roll. Webs may be films, nonwovens, laminates, apertured laminates, etc. The face of a web refers to one of its two dimensional surfaces, as opposed to its edge.

"X-Y plane" means the plane defined by the MD and CD of a moving web or the length.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

The present invention will be described with respect to a method and apparatus used for making an elastomeric apertured web. The apertured web can be an apertured film or an apertured laminate comprising a film and nonwoven. The apertured web is elastomeric. Apertures can include micro apertures and macro apertures, the former being substantially invisible to the unaided naked eye of an observer from approximately 1 meter away in ordinary indoor lighting and the latter being visible under such conditions. Micro apertures and/or other embossing or texturing can be formed prior to processing by the apparatus of the present invention. Aperture size may increase when a strain is induced in the web via the application of a tensile force. The apertured web can be used in disposable absorbent articles such as bandages, wraps, incontinence devices, diapers, sanitary napkins, pantiliners, tampons, and hemorrhoid treatment pads, as well as other consumer products such as floor cleaning sheets, body wipes, and laundry sheets. In addition, webs of the present invention can be utilized as perforated webs in automotive, agricultural, electrical, or industrial applications.

The physical characteristics of the aperture web are defined by the average aperture size ($mm^2$) and percent open area as measured according to the Aperture Size and Open Area Test described below. The average aperture size can be between 0.05 and 10 $mm^2$ Preferably the aperture size can be between 0.07 and 5 $mm^2$, and even more preferably between 0.10 and 2.5 $mm^2$ The percent open area can be between 0.1 and 10%, preferably between 0.2 and 5% and even more preferably between 0.3 and 2.5%.

One apparatus 150 of the present invention is shown schematically in FIG. 1. As shown in FIG. 1, web 1 can be formed from a generally planar, two dimensional precursor web 20 having a first surface 12 and a second surface 14. Precursor web 20 can be a polymer film or a laminate of a polymer film and a nonwoven web. First surface 12 corresponds to a first side of precursor web 20, as well as a first side of web 1. Second surface 14 corresponds to a second side of precursor web 20, as well as a second side of web 1. In general, the term "side" is used herein in the common usage of the term to describe the two major surfaces of generally two-dimensional webs, such as films. Of course, in a composite or laminate structure, the first surface 12 of the web 1 is the first side of one of the outermost layers or plies, and the second surface 14 is the second side of the other outermost layer or ply.

As shown in FIG. 1, precursor web 20 is moved in a machine direction (MD) to activation member 130 for incrementally stretching the precursor web and then on to forming apparatus 100 for forming apertures therein. Machine direction (MD) refers to the direction of travel for precursor web 20 as is commonly known in the art of making or processing web materials. Likewise, cross machine direction (CD) refers to a direction perpendicular to the MD, in the plane of precursor web 20.

Precursor web 20 can be provided either directly from a web making process or indirectly from a supply roll 152, as shown in FIG. 1. Precursor web 20 can be a composite or a laminate of two or more precursor webs, and can comprise, for example, a combination of polymeric films and nonwoven webs.

Polymeric film webs can comprise elastic materials, such as elastic polypropylene based films. A suitable film which can be utilized in an outer cover includes a 0.5-1.0 mil (0.0005-0.001") thick Vistamaxx® (elastomeric polypropylene) from ExxonMobil. Suitable elastomeric polypropylene based compositions are also disclosed in WO 2005/052052 to ExxonMobil and in WO 2005/097031 to Procter & Gamble. The elastomeric composition may also include fillers like titanium dioxide for improving opacity and calcium carbonate for breathability. Elastomeric polypropylenes may also be blended with styrenic block copolymers, semicrystalline polyolefins or sub-micron inorganic particles.

Nonwoven webs or fabrics have been formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond (SMS) webs and the like (e.g., SMMS, SSMS) made by multiple beam spunbond processes, can be utilized. It is not necessary that each component (i.e., the spunbond or meltblown components) be the same polymer. Therefore, in an SMS web, it is not necessary that the spunbond and the meltblown layers comprise the same polymer.

The constituent fibers of nonwoven webs can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from 0.1-500 microns in 1 micron increments.

Precursor web 20 can comprise a zero strain laminate comprised of at least two plies of material which are secured to one another, either intermittently or substantially continuously, along at least a portion of their coextensive surfaces while in a substantially untensioned ("zero strain") condition. At least one of the plies is preferably in the form of a continuous web to facilitate continuous, high speed processing. The other of the plies may comprise a continuous web or discrete elements or patches secured to the continuous web at predetermined locations. One of the plies employed in a zero-strain laminate web comprises a material which is elastomeric (e.g. elastic film). The second ply secured to the elastomeric ply is extensible. The second ply will, upon elongation, be at least to a degree permanently elongated so that upon release of the applied tensile forces, it will not fully return to its original undistorted configuration.

Precursor webs comprising a zero strain laminate can be mechanically activated or incrementally stretched (e.g. by ring rolling) to form an elastomeric laminate prior to aperturing the laminate. The formation of the apertures in the elastomeric laminate subsequent to activation via the incremental stretching process can reduce the tendency of the apertures to function as initiation points for tearing and failure of the web when strain is induced in the web during subsequent processing or use (e.g., during application of the article to a wearer or the wearing process itself).

Activation Member

In order to produce an elastomeric precursor web from a zero strain laminate, the precursor web can be incrementally stretched via activation member 130 prior to passing through the forming apparatus 100 shown in FIG. 1. As used herein, the term, "incremental stretching", also referred to as ring rolling, is a process in which a web is supported at closely spaced apart locations and then the unsupported segments of the web between these closely spaced apart locations are stretched. This can be accomplished by passing the web through a nip formed between a pair of meshing corrugated rolls, which have an axis of rotation perpendicular to the direction of web travel. Incremental stretching rolls designed for machine direction and cross direction stretching are described in U.S. Pat. No. 4,223,059.

Figure 2:
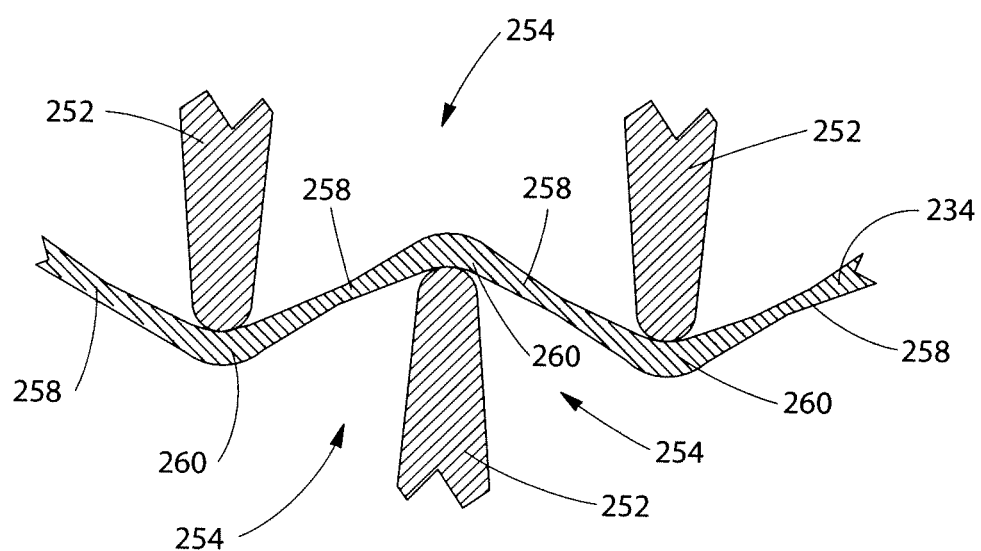
FIG. 2 is a cross-sectional representation of a portion of an incremental stretching apparatus.

FIG. 2 is an enlarged, fragmentary, cross-sectional view showing the interengagement of teeth 252 and grooves 254 of respective opposing activation rolls in a nip which incrementally stretch a web 234 of material therebetween. As shown, a portion of a web 234, which can be a zero strain laminate, is received between the interengaged teeth and grooves. The interengagement of the teeth and grooves causes laterally spaced portions of web 234 to be pressed by teeth 252 into opposed grooves 254. In the course of passing between activation rolls, the forces of teeth 252 pressing web 234 into opposed grooves 254 impose within web 234 tensile stresses that act in the machine or cross machine direction depending on the orientation of the teeth and grooves on the rolls. The tensile stresses can cause intermediate web sections 258 that lie between and that span the spaces between the tips of adjacent teeth 252 to stretch or extend in a machine or cross machine direction, which can result in a localized reduction of the web thickness at each of intermediate web sections 258. For nonwoven webs, the stretching can cause fiber reorientation, a reduction in basis weight, and controlled fiber destruction in the intermediate web sections 258.

Although the portions of web 234 that lie between the adjacent teeth are locally stretched, the portions of the web that are in contact with the tips of the teeth may not undergo a similar degree of extension. Because of the frictional forces that exist between the surfaces at the rounded outer ends of teeth 252 and the adjacent areas 260 of web 234 that are in contact with the tooth surfaces at the outer ends of the teeth, sliding movement of those portions of the web surfaces relative to the tooth surfaces at the outer ends of the teeth is minimized. Consequently, in some cases, the properties of the web 234 at those areas of the web that are in contact with the surfaces of the tooth tips change only slightly, as compared with the change in web properties that occur at intermediate web sections 258.

Some materials including polypropylenes, polyethylenes and polyesters are unable to withstand the high rate of strain involved with incremental stretching in commercial production. Such materials can be incrementally stretched at a low rate of strain according to the process apparatus described in U.S. Published Application No. 2008/0224351 A1. The publication describes a method and apparatus which uses activation members for incrementally stretching a web at a relatively low strain rate. The activation members include an activation belt and a single activation member wherein the activation belt and single activation member comprise a plurality of teeth and grooves that complement and engage one another at a depth of engagement in a deformation zone. The depth of engagement is capable of increasing linearly over the deformation zone. In exemplary embodiments the deformation zone can be controlled to increase linearly over at least a portion of the deformation zone such that a web interposed between the activation belt and the single activation member in the deformation zone is incrementally stretched at a low rate of strain.

Forming Apparatus

Subsequent to incremental stretching the precursor web forming an elastomeric precursor web, the elastomeric precursor web continues in the machine direction by means known in the art, including over or around any of various idler rollers, tension-control rollers, and the like (all of which are not shown) to the nip 116 of forming apparatus 150 formed by a pair of counter-rotating, intermeshing rolls 102 and 104. The pair of intermeshing rolls 102 and 104 operate to form apertures in web 20 forming apertured web 1. Intermeshing rolls 102 and 104 are more clearly shown in FIG. 3.

Figure 3:
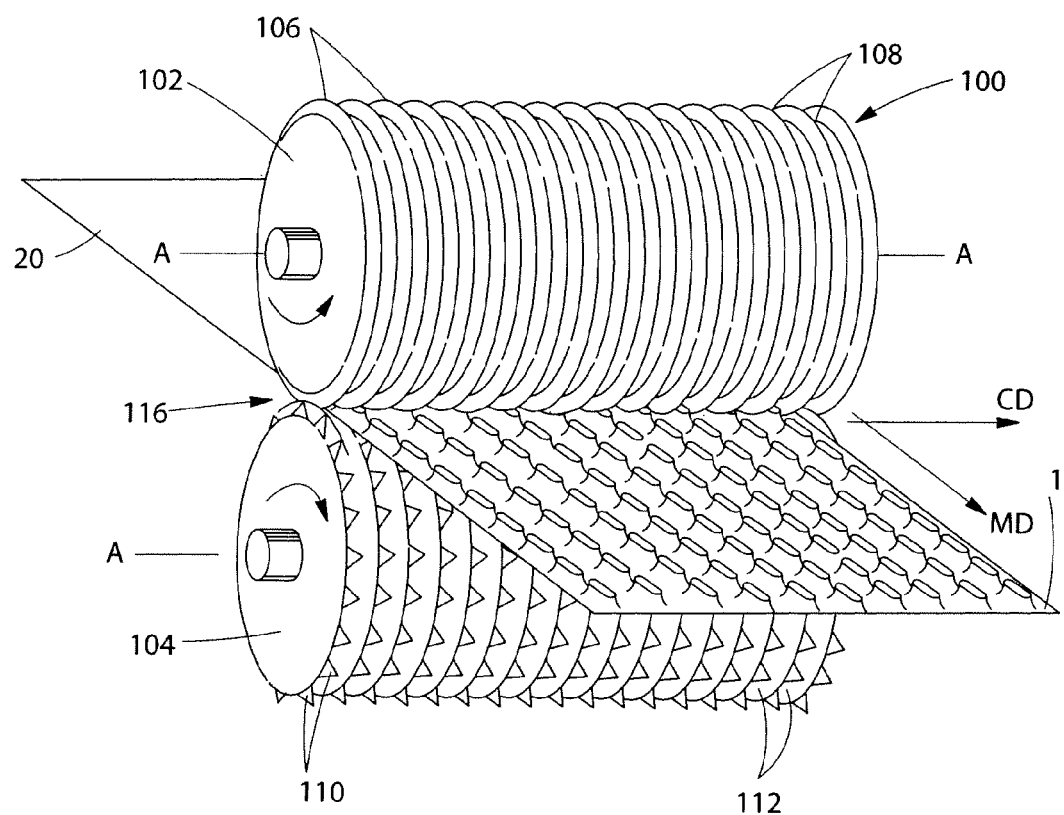
FIG. 3 is perspective representation of a forming apparatus of the present invention.
Figure 4:
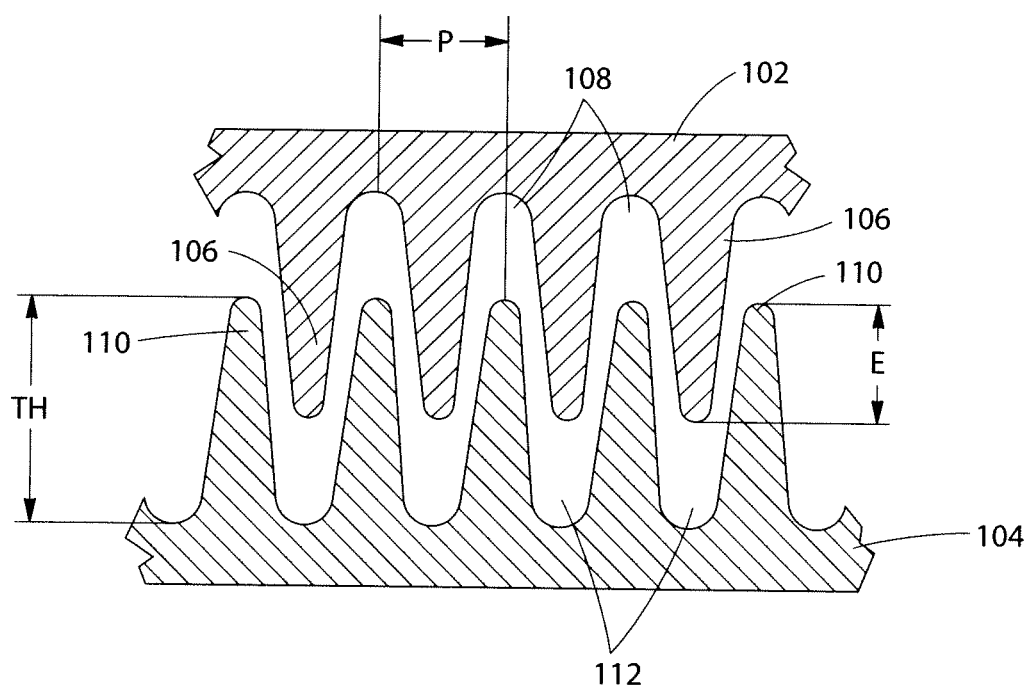
FIG. 4 is a cross-sectional representation of a portion of the apparatus shown in FIG. 3.

Referring to FIG. 3, there is shown in more detail the portion of forming apparatus 150 for making apertures in apertured web 1. This portion of apparatus 150 is shown as forming apparatus 100 in FIG. 3, and comprises a pair of steel intermeshing rolls 102 and 104, each rotating about an axis A, the axes A being parallel and in the same plane. Forming apparatus 100 can be designed such that precursor web 20 remains on roll 104 through a certain angle of rotation, as shown in detail below with respect to FIG. 4, but FIG. 3 shows in principle what happens as precursor web 20 goes straight through nip 116 on forming apparatus 100 and exits as apertured web 1. Therefore, while FIG. 3 shows apertured web 1 going straight into and coming straight out of nip 116, precursor web 20 or apertured web 1 can be partially wrapped on either of rolls 102 or 104 through a predetermined angle of rotation prior to (for precursor web 20) or after (for apertured web 1) nip 116. For example, after exiting nip 116, apertured web 1 can be directed to be wrapped on roll 104 through a predetermined angle of rotation such that the apertures remain resting over, and "fitted" onto, teeth 110 of roll 104, as shown in FIG. 4.

Rollers 102 and 104 can be made of steel or aluminum. In one embodiment, the rollers can be made of stainless steel. In general, rollers 102 and 104 can be made of corrosion resistant and wear resistant steel.

Roll 102 can comprise a plurality of ridges 106 and corresponding grooves 108 which can extend unbroken about the entire circumference of roll 102. In some embodiments, depending on what kind of pattern is desired in web 1, roll 102 can comprise ridges 106 wherein portions have been removed, such as by etching, milling or other machining processes, such that some or all of ridges 106 are not circumferentially continuous, but have breaks or gaps. The breaks or gaps can be arranged to form a pattern, including simple geometric patterns such as circles or diamonds, but also including complex patterns such as logos and trademarks. In one embodiment, roll 102 can have teeth, similar to the teeth 110 on roll 104, described more fully below. In this manner, it is possible to have three dimensional apertures having portions extending outwardly on both sides of apertured web 1. In addition to apertures, various out-of-plane macro-areas of apertures of web 1 can be made, including macro-patterns of embossed texture depicting logos and/or designs. In an alternate embodiment, the outer surface of roll 102 can comprise a brush or elastic material such as rubber which allow teeth on mating roll 104 to penetrate at a nip formed between the two rolls.

Alternatively, roll 102 may be replaced with a brush conveyor as disclosed in U.S. Pat. No. 5,802,682 issued to Jourde, et al. Sep. 8, 1998. For this embodiment the brush conveyor may be arranged to interface with the teeth on mating roll 104 such that the teeth penetrate the brush at a nip formed between roll 104 and the brush conveyor.

Roll 104 is similar to roll 102, but rather than having ridges that can extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 8, discussed below. Both or either of rolls 102 and 104 can be heated by means known in the art such as by incorporating hot oil filled rollers or electrically-heated rollers. Alternatively, although heating may not be required for stretchable webs, both or either of the rolls may be heated by surface convection or by surface radiation.

Teeth 110 can be joined to roller 104. By "joined" is meant that teeth can be attached to, such as by welding, compression fit, or otherwise joined. However, "joined" also includes integral attachment, as is the case for teeth machined by removing excess material from roller 104. The location at which teeth 110 are joined to roller 104 is the base. At any cross-sectional location parallel to the base each tooth can have a non-round cross-sectional area. In the circumferential direction a cross-sectional length of the cross-sectional area (corresponding to the tooth length, as discussed below), is at least two times a cross sectional width, measured perpendicular to the length dimension at the center of the cross-sectional area. In an alternate embodiment the teeth may comprise pins that are cylindrical, conical, rectangular, hexagonal, or other shapes depending on the corresponding aperture shape desired.

FIG. 4 shows in cross section a portion of the intermeshing rolls 102 and 104 including ridges 106 and representative teeth 110. As shown, teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of apertured web 1 of the present invention. For example, in general, to obtain a higher density of volcano-shaped structures 8 or apertures 6 of web 1, the smaller the pitch should be, and the smaller the tooth cross sectional length TL and tooth spacing distance TD should be, as described below.

It is also contemplated that the size, shape, orientation and spacing of the teeth 110 can be varied about the circumference and width of roll 104 to provide for varied apertured web 1 properties and characteristics.

Additionally, substances such as lotions, ink, surfactants, and the like can be sprayed, coated, slot coated, extruded, or otherwise applied to apertured web 1 before or after entering nip 116. Any processes known in the art for such application of treatments can be utilized.

After apertured web 1 is formed, it can be taken up on a supply roll 160 for storage and further processing as a component in other products. Or apertured web 1 can be guided directly to further post processing, including incorporation into a finished product, such as a disposable absorbent product.

Figure 5:
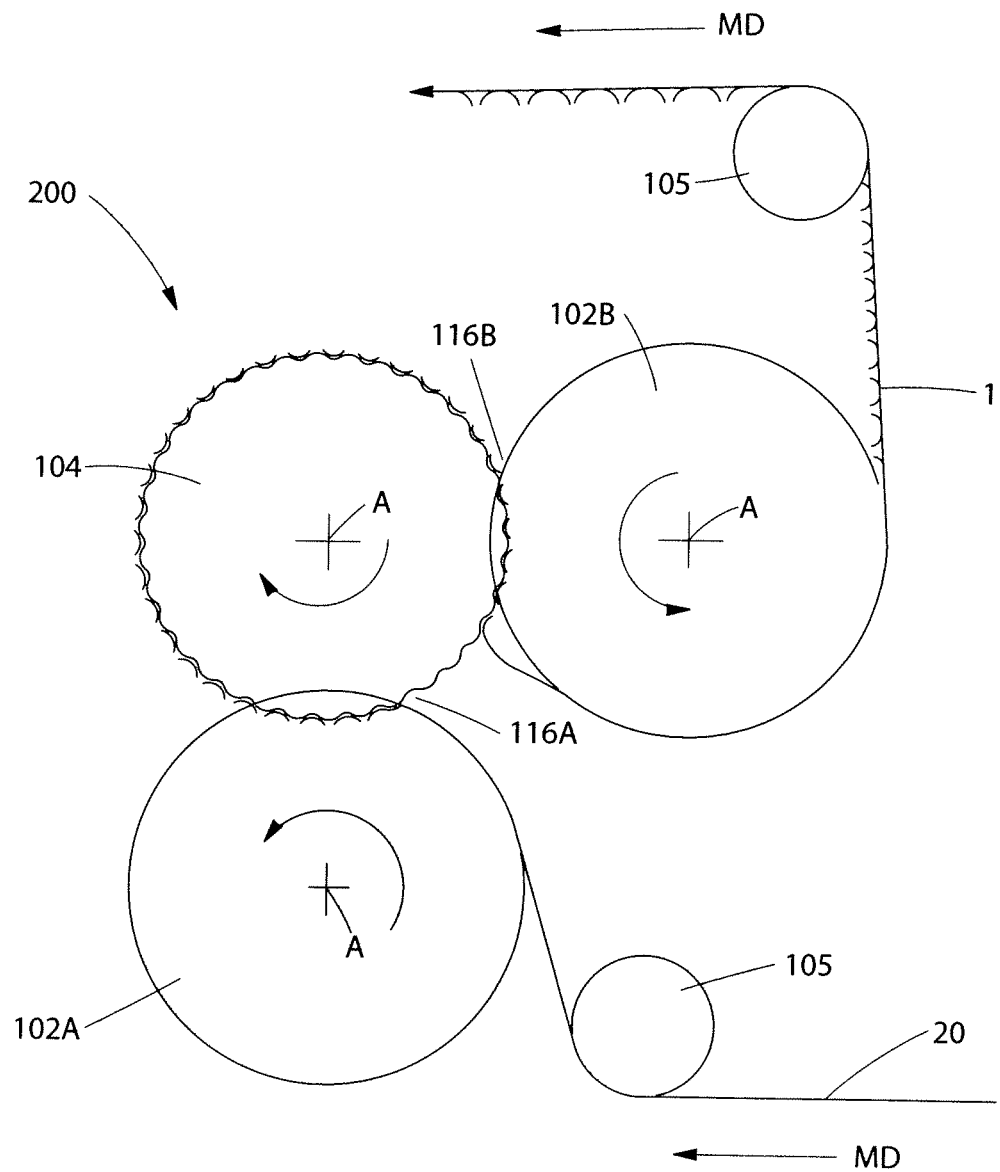
FIG. 5 is a schematic representation of another embodiment of a process and apparatus of the present invention.

In one embodiment, web 1 can be formed by processing a precursor web 20 through an apparatus 200 as shown in FIG. 5. The multi-roller arrangement of apparatus 200 is designed to provide for a predetermined dwell time in which apertured web 1 remains in contact with toothed roller 104 through a predetermined angle of rotation. While the angle of rotation can be optimized depending upon the type of film, temperature of rollers, and the speed of web travel, in general the angle of wrap can be at least 10 degrees and as high as about 270 degrees or more, depending, at least in part, on the relative sizes of the mating rollers. As shown, precursor web 20 can be guided around various guide rollers and tensioning members (not shown) to guide roller 105 and onto roll 102A which can have ridges and grooves as described with respect to roller 102 of apparatus 150 in FIG. 1 above. Roller 102A can be heated to aid in forming volcano-shaped structures 8 and apertures 6. In one embodiment, roller 102 can be heated to about 200° F.

As shown in FIG. 5, precursor web 20 enters nip 116A formed by the inter-engagement of meshing rollers 104 and 102A. Roller 104 of apparatus 200 can be a toothed roller as described above with respect to apparatus 150 in FIG. 1. As precursor web 20 passes through nip 116A, teeth 110 on roller 104 press into and/or through and can pierce precursor web 20 to form volcano-shaped structures 8 and apertures 6. Apertured web 1 then continues in stationary contact with rotating roller 104 until reaching nip 116B formed by the inter-engagement of roller 104 with roller 102B. Roller 102B can have ridges and grooves as described with respect to roller 102 of apparatus 150 in FIG. 1 above.

As web 1 exits nip 116B it is directed off of roller 104, onto roller 102B and over various guide rollers 105 as necessary before being wound for further processing, shipping, or placement for incorporation in a manufactured product. In one embodiment, web 1 is directed into a manufacturing process for disposable absorbent articles, wherein web 1 is fed into the process as a cover sheet and joined to other components such as a topsheet web, cut to finished shape, packaged, and shipped to retail outlets. In another embodiment, the web is directed into a manufacturing process for a diaper product, wherein web 1 is fed into the process as a backsheet and joined to other components such as a topsheet.

If web 1 tends to stick to teeth 110 upon being pulled off of roller 104, various processing aids can be added as necessary. For example, non-stick treatments, such as silicone or fluorocarbon treatments can be added. Various lubricants, surfactants or other processing aids can be added to the precursor web 20 or to the roller 104. Other methods of aiding the removal of the web from the roller include air knives or brushing. In one embodiment, roller 104 can have an internal chamber and means to provide positive air pressure at the point of web removal onto roller 102B. In general, control of the transition from roller 104 to roller 102B is affected by web speed, relative roller speeds (i.e., tangential speed of roller 104 and roller 102B), web tension, and relative coefficients of friction. Each of these parameters can be varied as known by those skilled in the art to ensure the desired transfer of web 1 onto roller 102B.

The benefit of having an apparatus like that shown in FIG. 5 is that web 1 experiences an extended amount of time in contact with and "nested" on teeth 110 of roller 104. In this manner, volcano-shaped structures 8 and apertures 6 have additional time to set and a higher likelihood of retaining a three-dimensional configuration once removed from roller 104. Without being bound by theory, it is believed that by adjusting the circumference of roller 104, the temperature of rollers 102A, 104, and/or 102B, as well as the coefficient of friction of rollers, this longer dwell time can be used to increase the line speed at which web 1 can be processed to make permanent three-dimensional volcano-shaped structures 8. The temperature of rollers 102A, 104, and/or 102B may all be at the same temperature or alternatively at different temperatures. The rollers may be heated to a particular temperature or unheated and at approximately ambient temperature. For example, rollers 102A and 104 may be heated while roller 102B is at room temperature or below. In addition, the speeds of the various rollers may be maintained at the same speed, or alternately a speed differential between the rollers may be established.

If any of the rollers of the apparatus 150 or 200, as described above are to be heated, care must be taken to account for thermal expansion. In one embodiment, the dimensions of ridges, grooves, and/or teeth are machined to account for thermal expansion, such that the dimensions shown in FIG. 4 and dimensions described herein are dimensions at operating temperature.

Forming Apparatus Teeth

Figure 6:
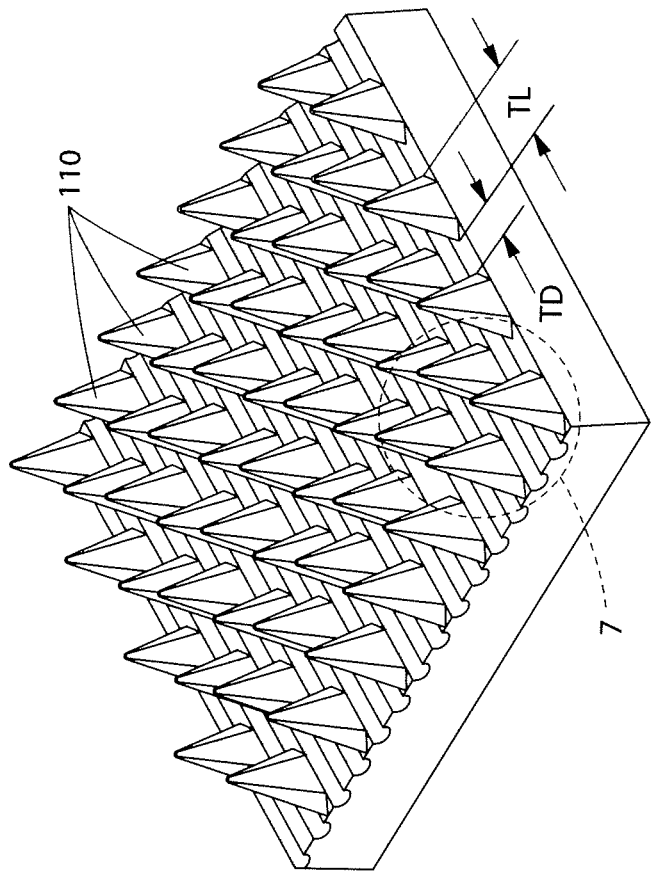
FIG. 6 is a perspective view of a portion of the apparatus shown in FIG. 3 or FIG. 5.
Figure 7:
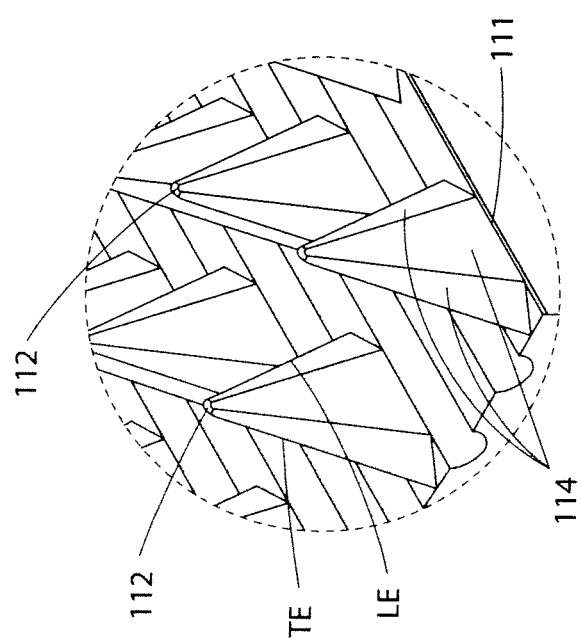
FIG. 7 is a magnified perspective view of a portion of the apparatus shown in FIG. 6.

FIG. 6 shows a portion of one embodiment of a roller 104 having a plurality of teeth 110 useful for making an apertured web 1. An enlarged view of the teeth 110 shown in FIG. 6 is shown in FIG. 7. As shown in FIG. 7, each tooth 110 has a base 111, a tooth tip 112, a leading edge LE and a trailing edge TE. The tooth tip 112 can be generally pointed, blunt pointed, or otherwise shaped so as to stretch and/or puncture the precursor web 20. Teeth 110 can have generally flattened blade-like shape. That is, as opposed to round, pin-like shapes that are generally round in cross section, teeth 110 can be elongated in one dimension, having generally non-round, elongated cross-sectional configurations. For example, at their base 111, the cross section of teeth 110 can have a tooth length TL and a tooth width TW exhibiting a tooth aspect ratio AR of TL/TW of at least 2, or at least about 3, or at least about 5, or at least about 7, or at least about 10 or greater. In one embodiment, the aspect ratio AR of cross-sectional dimensions remains substantially constant with tooth height.

In one embodiment of roller 104, teeth 110 can have a uniform cross sectional length dimension TL of about 1.25 mm measured generally from the leading edge LE to the trailing edge TE at the base 111 of the tooth 110, and a tooth cross sectional width TW of about 0.3 mm measured generally perpendicularly to the circumferential length dimension at the base. Teeth can be uniformly spaced from one another circumferentially by a distance TD of about 1.5 mm. For making a soft, fibrous three-dimensional apertured web 1 from a precursor web 20 having a basis weight in the range of from about 5 gsm to about 200 gsm, teeth 110 of roll 104 can have a length TL ranging from about 0.5 mm to about 3 mm, a tooth width TW of from about 0.3 mm to about 1 mm, and a spacing TD from about 0.5 mm to about 5 mm, a tooth height TH ranging from about 0.5 mm to about 10 mm, and a pitch P between about 1 mm (0.040 inches) and 3 mm (0.100 inches). Depth of engagement E can be from about 0.5 mm to about 5 mm (up to a maximum approaching the tooth height TH).

Of course, depth of engagement E, pitch P, tooth height TH, spacing TD and tooth cross sectional length TL can each be varied independently of each other to achieve a desired size, spacing, and area density of apertures 6 (number of aperture 6 per unit area of apertured web 1). For example, to make apertured films and nonwovens suitable for use in sanitary napkins and other absorbent articles, tooth cross sectional length TL at the base can range between about 2 mm to about 3.81 mm; tooth width TW can range from about 0.508 mm to about 1.27 mm; tooth spacing TD can range from about 1.0 mm to about 4.0 mm; pitch P can range from about 1.106 mm to about 2.54 mm; and tooth height TH can be from about 2.0 mm to about 9.0 mm. Depth of engagement E can be from about 0.5 mm to about 5 mm. The radius of curvature R of the tooth tip 112 can be from 0.07 mm to about 0.4 mm. Without being bound by theory, it is believed that tooth length TL at the base can range between about 0.254 mm to about 12.7 mm; tooth width TW can range from about 0.254 mm to about 5.08 mm; tooth spacing TD can range from about 0.0 mm to about 25.4 mm (or more); pitch P can range from about 1.106 mm to about 15.0 mm; tooth height TH can range from 0.254 mm to about 18 mm; and depth of engagement E can range from 0.254 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

Without wishing to be bound by theory, and consistent with currently-pending tool designs, it is believed that other dimensions are possible for use in the method and apparatus of the present invention. For example, tooth length TL at the base can range from about 0.254 mm to about 12.7 mm, and can include 2.03 mm, 4.42 mm, 4.572 mm and about 5.56 mm; tooth width TW can range from about 0.254 mm to about 5.08 mm, and can include 0.63 mm, 0.84 mm, and 1.78 mm; tooth spacing TD can range from about 0.0 mm to about 25.4 mm, and can include 2.032 mm and 3.68 mm; pitch P can range from about 1.106 mm to about 7.62 mm and include 2.54 mm; tooth height TH can range from 0.254 mm to about 18 mm, and can include 5.08 mm and 8.2 mm; and depth of engagement E can range from 0.254 mm to about 6.35 mm. Radius of curvature can range from about 0.00 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments). The teeth may be arranged on a rotating roll having a width of between about 10 mm and 1000 mm or more, and a diameter of between about 50 mm and 1000 mm, including 144 mm. The roll may rotate during the aperturing process at a tangential speed of between about 10 and 1000 m/min.

In one embodiment, to make the volcano-shaped structures 8 and/or apertures 6 of apertured web 1, the LE and TE should taper to a point in a generally pyramidal or frustro-conical shape which can be described as being shaped like a shark's tooth. As shown in FIG. 7, the generally pointed pyramidal shark tooth shape can have six sides 114, each side being generally triangular in shape. The vertex of two sides makes up the leading edge LE and the vertex of two sides makes up the trailing edge TE of tooth 110. The vertices of the leading or trailing edge can be relatively sharp, or can be machined to have a rounded radius of curvature. The radius of curvature of the tooth tip can be 0.005 inches.

Figure 8:
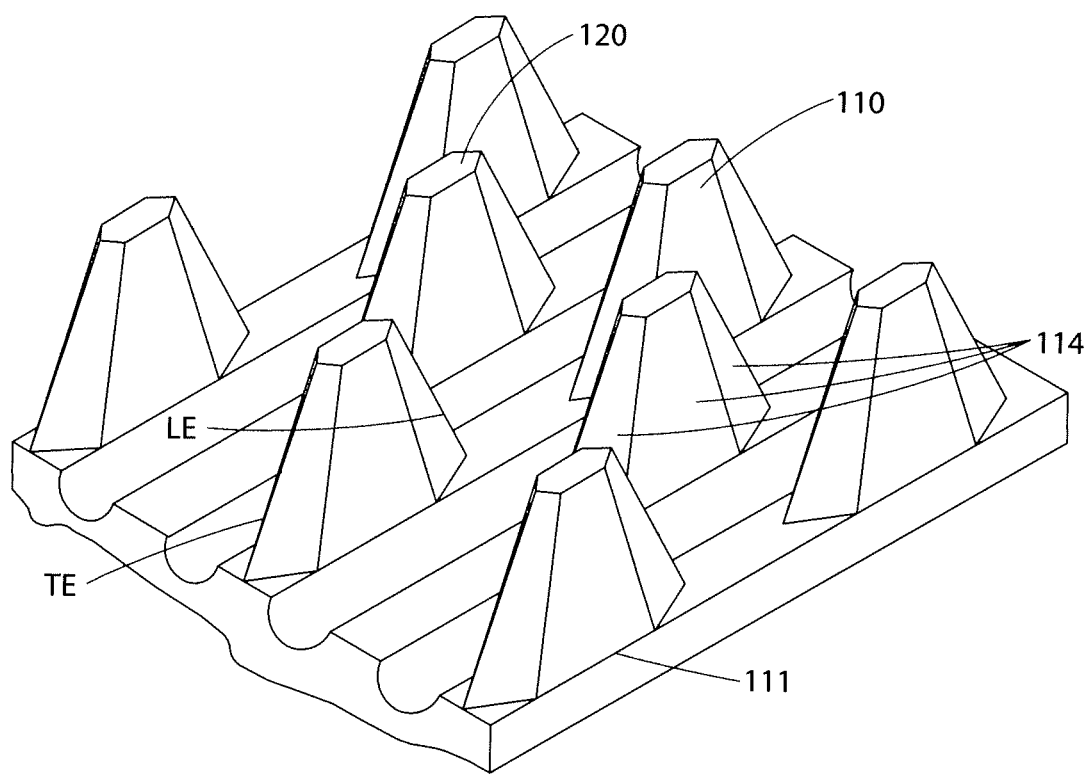
FIG. 8 is a perspective view of an alternative configuration for teeth on the apparatus shown in FIG. 3.

Other tooth shapes can be utilized to make apertures. As shown in FIG. 8, for example, the generally pyramidal shapes shown in FIG. 6 can be truncated so as to remove the pointedness of tips 112. Truncation can be made at a predetermined distance from base 111 such that a generally flattened region 120 is produced at the distal end of tooth 110. Generally flattened region 120 can have an area shape corresponding to the cross-sectional shape of tooth 110. Thus, generally flattened region 120 can also be elongated, that is, having a length dimension greater than a width dimension and an aspect ratio AR corresponding to the aspect ratio of tooth 110. In one embodiment, flattened region 120 can transition to sides 114 at generally sharp vertices, or the transition can be at a radius of curvature, providing for a smooth, rounded, flattened tooth tip.

Figure 9:
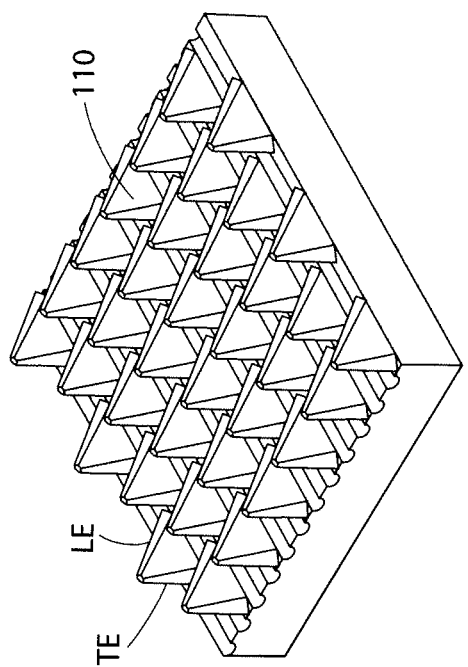
FIG. 9 is a perspective view of an alternative configuration for teeth on the apparatus shown in FIG. 3.

In another embodiment, as shown in FIG. 9, teeth 110 can have at least one edge that extends generally perpendicularly with respect to the surface of roller 104. As shown in the partial perspective view of roller 104 in FIG. 9, for example, teeth resembling shark fins can have a leading edge LE that angles toward tip tooth 112, and a trailing edge TL that extends generally perpendicular from base 111 toward tip tooth 112. In another embodiment, the tooth 110 can have the same shape, but the leading and trailing edges reversed such that the generally perpendicular edge is the leading edge.

Figure 10:
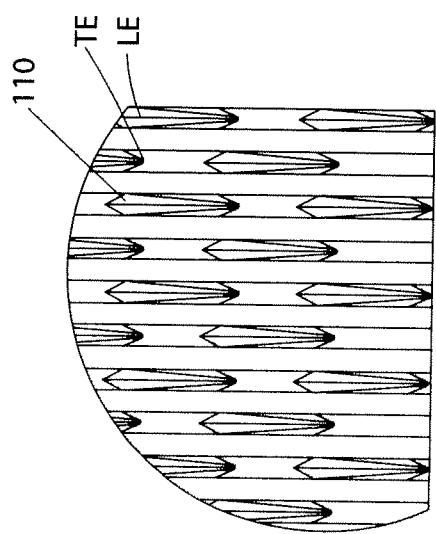
FIG. 10 is a top view of the portion of the apparatus shown in FIG. 9.
Figure 11:
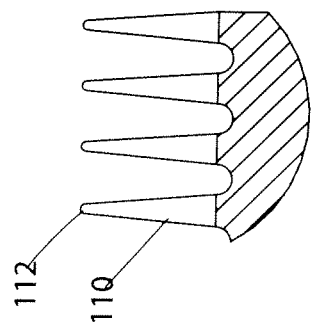
FIG. 11 is a side view of the teeth shown in FIG. 9.

FIG. 10 is a top view of the portion of roller 104 shown in FIG. 9. Various dimensions are shown in the illustrated embodiment, including the angles produced by the sides 114 making up the leading and trailing edges. Likewise, FIG. 11 is a detail of the teeth shown in FIG. 9 showing representative dimensions. In general, while the dimensions shown are those currently believed to be beneficial for making three-dimensional formed films useful as topsheets on disposable absorbent articles, all dimensions can be varied as necessary depending on the desired aperture density, spacing, size, and the web type of precursor web 20.

Without being bound by theory, it is believed that having relatively sharp tips on teeth 110 permits the teeth 110 to punch through precursor web 20 "cleanly", that is, locally and distinctly, so that the resulting web 1 can be described as being predominantly "apertured" rather than predominantly "embossed". In one embodiment, puncture of precursor web 20 is clean with little deformation of web 20, such that the resulting web is a substantially two-dimensional perforated web.

It is contemplated that the size, shape, orientation and spacing of the teeth 110 can be varied about the circumference and width of roll 104 to provide for varied apertured web 1 properties and characteristics. The number, spacing, and size of apertures 6 can be varied by changing the shape, number, spacing, and size of teeth 110 and making corresponding dimensional changes as necessary to roll 104 and/or roll 102. This variation, together with the variation possible in precursor webs 20 and the variation in processing, such as line speeds, roll temperature, and other post processing variations, permits many varied apertured webs 1 to be made for many purposes.

The apertured web according to the present invention can be incorporated into an absorbent article such as a diaper as a dampness management means. The dampness management means can be an outer cover providing leakage protection while at the same time permitting vapors to escape from the diaper while still preventing exudates from passing through the outer cover. The aperture web according to the present invention can also be incorporated into an absorbent article such as a diaper as a stretchable outer cover that does not need to provide dampness management function. In such a design the core bucket, which comprises a breathable backsheet, a topsheet and an absorbent core in between, provides all the fluid handling functions (i.e. urine and BM).

In another embodiment, the dampness management means may include zones of different breathability and/or liquid permeability. For example, the dampness management means may be higher in breathability and/or liquid permeability in zones which do not coincide with the absorbent core. As used herein, the term "breathability" refers to the diffusive transport of water vapor through the material. The dampness management means may be assembled of one or more layers and preferably includes at least one layer which is liquid impermeable, the liquid impermeable layer preferably located adjacent the absorbent core and preferably covers an area at least as large as the absorbent core.

A distinct benefit of the apparatus 150 or 200 as described above for forming apertured webs for use in disposable absorbent articles is the ability to adapt and position the apparatus 150 or 200 as a unit operation in an existing process for making such articles. For example, apertured web 1 can be a backsheet outer cover in an absorbent article such as a disposable diaper. Rather than make the apertured web off line, perhaps at a geographically remote location, apertured web 1 can be made on line by putting forming apparatus 150 in line with the supply of stretchable outer cover material on a production line for making disposable diapers or pants. Doing so provides several distinct advantages. First, having forming apparatus 150 making apertures in the outer cover directly on the diaper production line eliminates the need to purchase apertured webs, which can be costly when made by traditional processes. Second, toothed roll 104 can be configured such that toothed regions are made in predetermined patterns, so that the apertured portion of an apertured backsheet outer cover is formed in a predetermined pattern. For example, an outer cover can be made on line in which the apertures are only disposed in the waist region, hip region, crotch region, or core region, or any combination of the above. Further, the outer cover can be made having different aperture densities, shapes, sizes, or any combination thereof, in different regions of the outer cover. For example, the aperture density proximate the longitudinal centerline of the outer cover may be higher than the aperture density distal to the longitudinal centerline. Likewise, apertures can be formed such that apertured regions are registered with other visible components, including channels, indicia, color signals, and the like.

EXAMPLE

The laminate used in forming the elastomeric apertured web comprises an 18 gsm 70/30 PP/PE spunbond bicomponent outer nonwoven layer that is adhesively laminated to an extrusion bilaminate comprising a 22 gsm VISTAMAXX film (with a 3 gsm PE based skin) that is laminated to an 18 gsm 50/50 PP/PE spunbond bicomponent nonwoven. The two nonwovens can be obtained from Fiberweb, Simpsonville, S.C. under the trade name SOFTEX. VISTAMAXX, an elastomeric polypropylene resin, is available from Exxon Mobil Chemical, Houston, Tex. The bilaminate of VISTAMAX film and SOFTEX nonwoven can be obtained from Clopay, Cincinnati, Ohio. An adhesive used in bonding the laminates includes H2861 (spiral pattern, basis weight=9 gsm) supplied by Bostik Findley, Wauwatosa, Wis.

The laminate is mechanically activated to form an elastomeric web material prior to passing through a forming apparatus. The forming apparatus has the following characteristics:

Tooth shape=hexagonal
Tooth length at base=2.034 mm
Tooth width at base=0.84 mm
Tooth height=8.2 mm
Tooth spacing=3.68 mm
Roll diameter=144.46 mm
Roll width=200 mm
Web speed/tangential roll speed=320 m/minute
Roll Temperature=Ambient (22° C.)
Depth of Engagement=0.120, 0.140 and 0.160 inches Table 1 below gives the Hysteresis Test and Breathability data for three apertured elastomeric webs, wherein the aperturing is done at 3 different DOEs. Table 2 gives the Average Aperture Size and Percent Open Area of the resulting elastomeric apertured webs measured at 10% strain.

TABLE 1

Hysteresis and Breathability

| Code | DOE (in.) | Hysteresis Test | | | | WVTR Test | |
|---|---|---|---|---|---|---|---|
| | | Load at 50% strain (N/cm) | | % set | | WVTR (gm/m2/day) | |
| | | Mean | Std. dev. | Mean | Std. dev. | Mean | Std. dev. |
| GRT296-068-1 | 0.120 | 0.30 | 0.02 | 4.07 | 1.56 | 1324 | 99 |
| GRT296-068-2 | 0.140 | 0.29 | 0.01 | 5.34 | 1.00 | 1520 | 184 |
| GRT296-068-3 | 0.160 | 0.47 | 0.05 | 4.73 | 0.20 | 1768 | 120 |

TABLE 2

Aperture Size and Open Area (sample stretched 10%)

| Code | DOE (in.) | Aperture Size & Open Area Test | | | |
|---|---|---|---|---|---|
| | | Average Aperture Size (mm$^2$) | | Percent Open Area | |
| | | Mean | Std. dev. | Mean | Std. dev. |
| GRT296-068-1 | 0.120 | 0.12 | 0.01 | 0.37 | 0.05 |
| GRT296-068-2 | 0.140 | 0.08 | 0.01 | 0.38 | 0.04 |
| GRT296-068-3 | 0.160 | 0.09 | 0.01 | 0.40 | 0.02 |

Test Methods

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed 2° C. and relative humidity of 50%±2%. The samples are conditioned for 24 hours prior to testing.

Hysteresis Test

1. Select a 2.54 cm (width)×7.62 cm (length) sample of the material for testing. In some cases, if it is not be possible to get a 2.54 cm×7.62 cm sample, a smaller sample may be used, but a gauge length of 25 mm must still be used. If the sample is activated or includes an activation portion, the length of the sample is taken in the direction of activation.
2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.
3. Calibrate the tester according to the manufacturer's instructions.
4. Set the distance between the grips (gauge length) at 25 mm.
5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.
6. a. First cycle loading: Pull the sample to a strain of 50% at a constant cross head speed of 254 mm/min.
   b. First cycle unloading: Hold the sample at 50% strain for 30 seconds and then return the crosshead to a position corresponding to the adjusted gauge length (0% strain) at a constant cross head speed of 254 mm/min. Hold the sample in the unstrained state for 1 minute.
   c. Set from second cycle loading: Pull the sample at a constant cross head speed of 254 mm/min, till it reaches a load of 0.05 N/25.4 mm (0.020 N/cm). Record the extended gauge length ($l_{ext}$). Next, return the crosshead to a position corresponding to the adjusted gauge length (0% strain) at a constant cross head speed of 254 mm/min, with no dwell time between extension and return. Set is defined as the maximum strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)
2. % set (Percent Strain measured at a second cycle load of 0.02N/cm); % set=$(l_{ext}-l_{ini})/l_{ini}*100\%$.

5 repetitions are done on each sample and the average and standard deviation reported.

Water Vapor Transmission Rate (WVTR) Test

The water vapor transmission rate is a measure of the rate at which water vapor flows through flexible barrier materials. WVTR is measured according to WSP 70.4 (08), which is the Standard Test Method for Water Vapor Transmission Rates of 500 to 100,000 gsm/day. The method is used to determine the WVTR of the apertured web. The Permatran-W model 100K was purchased from MOCON, Minnesota, Minn. The test method was run as per the WSP standard test, under the following conditions/settings:

1) Temperature of the test apparatus is set at 37.8 C.
2) The control knob in each cell needs to be adjusted to get a relative humidity (RH) of 60%+/−1.5%.
3) Test mode=standard for running the samples and the standard reference film; number of cycles=2; cycle time=5 minutes.
4) The standard reference film (S/N 1008WK089 from MOCON) should be run prior to testing the samples in order to ensure that the equipment is running properly. The standard reference film results should be within +/−10%.

Aperture Size and Open Area Test

Average aperture size (mm$^2$) and percent open area of the apertures (%) were measured by light microscopy with image analysis. A Nikon SMZ1500 microscope fitted with a 0.5× Nikon WD136 HR Plan Apo lens, and the stage illuminator was used. Magnification was set at 0.75× to give a viewing area of approximately 30×25 mm. Transmitted light Images were acquired using an Evolution MP Color Digital Camera (Media Cybernetics, Bethesda, Md.) and processed using ImageJ software version 1.42 (NIH, Bethesda, Md.). The specimen was stretched and then secured onto a rectangular Plexiglass frame (0.5 cm thick, 12.5×18.5 cm overall dimensions, inside opening of 7.5×12.5 mm) for viewing on the microscope. Stretch the sample 10% in the specified direction of stretch. If the direction of stretch is not specified, determine the direction of the stretch by gently pulling the edges of a scrap piece of the sample. The direction of the stretch is to be designated the lateral direction; the direction perpendicular is designated as the longitudinal direction. Cut a 15 cm×15 cm test specimen from the sample and prepare it for analysis as follows. Place the specimen face-up on a flat surface (e.g., lab bench). Along the top lateral edge, accurately measure and mark a 10 cm length centered at the midpoint of the specimen's edge. With masking tape, tape along the longitudinal sides of the specimen at those marks, to define a 10 cm (lateral) by 15 cm (longitudinal) test region. Secure the left longitudinal edge of the specimen to the bench using masking tape. Gently and uniformly extend the right side laterally such that the 100 mm wide test region is elongated to 110 mm in the lateral direction. Secure the right side of the specimen to the bench with masking tape. Affix the plexiglass frame, centered on the specimen, using two-sided tape. Remove the specimen from the bench, with the frame now securing the specimen in the extended condition.

Set the camera capture software to 8 bit grayscale. Turn the stage light on and place the specimen onto the microscope stage and focus the image. Remove the specimen and place a calibrated ruler on the stage. Take an image of the ruler for calibration of the images (top illumination is temporarily needed to image the ruler). The magnification and focus should not be changed after the calibration image is taken. Place the specimen back onto the stage and adjust the stage light until the holes are clearly illuminated. Collect five images at different positions along the surface of the specimen.

Load the images into ImageJ for analysis. Open the ruler image and calibrate the software for the number of pixels per mm of length. Next open a specimen image, and adjust contrast to give a black and white image. Apply a binary mask to invert the image to give black holes on a white background. Set the software to exclude holes that are in contact with the edges of the image. For calculation of average aperture size (not total open area), exclude any holes contained within the holes (fill holes), and exclude holes with an area less than 0.02 $mm^2$. Following these settings, calculate the average hole area and total open area of the holes. The average of the hole areas gives the average aperture size. Percent open area is the ratio of the total open area of the holes to the total area of the specimen times 100. Repeat this procedure with all five images of the specimen, and average the individual results. Report the averages to 2 decimal places.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a water vapor permeable elastomeric apertured web, the method comprising:
    a. providing a precursor web comprising a zero strain laminate comprising a substantially untensioned first elastomeric ply secured to a substantially untensioned second extensible ply comprising a continuous web;
    b. subjecting the precursor web to incremental stretching whereby the second ply is permanently elongated forming an elastomeric precursor web;
    c. providing a forming apparatus comprising a first member and a second member, wherein the first member comprises a mating member, and the second member comprises teeth being tapered from a base and a tip, the teeth being joined to the second member at the base, wherein said teeth are sized to form apertures in said precursor web, so that said apertured web will be water vapor permeable; and
    d. moving the elastomeric precursor web material through the forming apparatus, wherein apertures are formed in the elastomeric precursor web material as the teeth on the second member penetrate completely through the precursor web to form a water vapor permeable elastomeric apertured web.

2. The method of claim 1 wherein the forming apparatus comprises a pair of counter-rotating rollers, wherein the first member comprises a first roller and the second member comprises a second roller with the teeth arranged in rows, each row extending at least partially about a circumference of the second roller, wherein the elastomeric precursor web is moved through a nip formed between the counter-rotating rollers forming apertures in the elastomeric precursor web.

3. The method of claim 2 wherein the first roller comprises circumferentially-extending ridges and grooves which intermesh with the teeth on the second roller at the nip.

4. The method of claim 2 wherein the first roller comprises radially extending bristles forming a brush which interfaces with the teeth on the second roller at the nip.

5. The method according to claim 2 wherein the second roller is heated.

6. The method of claim 2, wherein the teeth are generally pyramid-shaped having at least six sides, the sides being substantially triangular and tapering to substantially a point.

7. The method of claim 2, wherein the teeth are integral projections of the second roller.

8. The method of claim 2, wherein the precursor web has a predominant molecular orientation that is in the machine direction and each tooth is oriented at an angle greater than about 30 degrees relative to the machine direction.

9. The method of claim 1 wherein elastomeric apertured web has a Water Vapor Transmission Rate of at least 1000 $g/m^2/day$.

10. The method of claim 1 wherein the method is a unit operation in a disposable absorbent article manufacturing process wherein the method further comprises the step of conveying the elastomeric apertured web to the disposable absorbent article manufacturing process wherein the elastomeric apertured web is converted to form an outer cover of a disposable absorbent article wherein the outer cover has a WVTR of at least about 1500 g/m$^2$/day.

11. The method of claim 1 wherein the first elastomeric ply is applied discretely to the second extensible ply.

12. The method of claim 11 wherein the first elastomeric ply is discontinuous in the cross machine direction.

13. A method for making a water vapor permeable elastomeric apertured web, the method comprising:
   a. providing a precursor web material comprising a zero strain laminate comprising a substantially untensioned first elastomeric ply secured to a substantially untensioned second extensible ply comprising a continuous web;
   b. subjecting the precursor web to incremental stretching whereby the second ply is permanently elongated forming an elastomeric precursor web;
   c. providing a forming apparatus; and
   d. moving the elastomeric precursor web material through the forming apparatus, wherein the forming apparatus penetrates completely through the web forming apertures therein, wherein said apertured web is water vapor permeable.

14. The method of claim 13 wherein the forming apparatus comprises pair of counter-rotating, intermeshing rollers forming a nip therebetween, wherein a first roller comprises circumferentially-extending ridges and grooves, and a second roller comprises radially extending penetrating members.

15. The method according to claim 14 wherein the penetrating members comprise teeth being tapered from a base and a tip, the teeth being joined to the second roller at the base, the base of the tooth having a cross-sectional length dimension greater than a cross-sectional width dimension.

16. The method according to claim 14 wherein the penetrating members comprise conical pins.

17. The method of claim 13 wherein the first elastomeric ply comprises a polymer film and the second ply comprises a nonwoven web.

18. The method of claim 13 wherein the elastomeric apertured web exhibits a WVTR of at least about 1000 g/m$^2$/day.

19. The method of claim 13 wherein the method is a unit operation in a disposable absorbent article manufacturing process wherein the method further comprises the step of conveying the apertured elastically extensible precursor web to the disposable absorbent article manufacturing process wherein the elastically extensible apertured precursor web is converted to form an outer cover of the disposable absorbent article wherein the outer cover has a WVTR of at least about 1500 g/m$^2$/day.

20. The method of claim 1 wherein the elastomeric apertured web comprises at least a zone that is breathable, and at least one layer that is liquid impermeable.

21. The method of claim 1 wherein the teeth of said second member of said forming apparatus are sized and configured to form apertures in said elastomeric precursor web material that have an average size between 0.05 mm$^2$; and 10 mm$^2$.

22. The method of claim 1 wherein the teeth of said second member of said forming apparatus are sized and configured to form microapertures in said elastomeric precursor web material.

23. The method of claim 1 wherein the teeth of said second member of said forming apparatus are sized and configured so that after forming the apertures in said elastomeric precursor web material, the water vapor permeable elastomeric apertured web is liquid impermeable.

* * * * *